(12) United States Patent
Danielson et al.

(10) Patent No.: US 8,506,591 B2
(45) Date of Patent: Aug. 13, 2013

(54) TISSUE FASTENERS AND RELATED INSERTION DEVICES, MECHANISMS, AND METHODS

(75) Inventors: Kenneth S. Danielson, Peacham, VT (US); Charles H. Rogers, Halifax, MA (US); Peter L. Stokes, Boston, MA (US); Edward R. Hall, Somerville, MA (US)

(73) Assignee: Opus KSD Inc., Peacham, VT (US)

( * ) Notice: Subject to any disclaimer, the term of this patent is extended or adjusted under 35 U.S.C. 154(b) by 919 days.

(21) Appl. No.: 12/305,071

(22) PCT Filed: Jun. 29, 2007

(86) PCT No.: PCT/US2007/015418
§ 371 (c)(1),
(2), (4) Date: Dec. 16, 2008

(87) PCT Pub. No.: WO2008/005465
PCT Pub. Date: Jan. 10, 2008

(65) Prior Publication Data
US 2009/0206127 A1   Aug. 20, 2009

Related U.S. Application Data

(60) Provisional application No. 60/817,858, filed on Jul. 1, 2006.

(51) Int. Cl.
*A61B 17/08* (2006.01)
*A61B 17/10* (2006.01)

(52) U.S. Cl.
USPC ............. 606/213; 606/142; 606/215; 227/19; 227/175.1

(58) Field of Classification Search
USPC .............. 606/104, 139, 142, 213, 215, 216, 606/219, 232, 300, 302, 304, 217, 148, 150; 227/19, 175.1, 175.2, 175.3, 175.4, 176.1, 227/177.1, 178.1, 179.1, 180.1, 181.1, 182.1
See application file for complete search history.

(56) References Cited

U.S. PATENT DOCUMENTS 2,206,460 A * 7/1940 Hansen .......................... 227/132
3,875,648 A   4/1975 Bone
(Continued)

FOREIGN PATENT DOCUMENTS

| EP | 0589306 A2 | 3/1994 |
| WO | 03071962 A2 | 9/2003 |
| WO | 2008005465 A2 | 1/2008 |

OTHER PUBLICATIONS

Written Opinion of the International Searching Authority for corresponding international application No. PCT/US07/15418, issued Jan. 1, 2009, 3 pages.
(Continued)

*Primary Examiner* — Darwin Erezo
*Assistant Examiner* — Jing Ou
(74) *Attorney, Agent, or Firm* — Brown Rudnick LLP

(57) ABSTRACT

A tissue fastener includes a bridge section and two cannulated leg sections. The tissue fastener is a single piece of material, and the material can be a bioabsorbable material. Each of the two leg sections can include at least one barb for resisting dislodgement from tissue after the fastener is inserted into tissue. The bridge can be flexible, and the leg sections can receive needles to allow insertion of the fastener into tissue from above a surface of the tissue. Various insertion devices and mechanisms are possible to deploy the fastener into a wound in a patient's skin from above the surface of and generally perpendicular to the skin.

10 Claims, 20 Drawing Sheets

(56) References Cited

U.S. PATENT DOCUMENTS

| | | | | |
|---|---|---|---|---|
| 4,179,063 A | | 12/1979 | Russell | |
| 4,410,125 A | * | 10/1983 | Noiles et al. | 227/19 |
| 4,627,437 A | | 12/1986 | Bedi et al. | |
| 4,669,473 A | | 6/1987 | Richards et al. | |
| 4,736,746 A | | 4/1988 | Anderson | |
| 4,994,073 A | | 2/1991 | Green | |
| 5,089,009 A | | 2/1992 | Green | |
| 5,269,783 A | | 12/1993 | Sander | |
| RE34,891 E | | 4/1995 | Kunreuther | |
| 5,466,243 A | | 11/1995 | Schmieding et al. | |
| 5,584,859 A | | 12/1996 | Brotz | |
| 5,615,816 A | | 4/1997 | Deschenes et al. | |
| 5,641,234 A | * | 6/1997 | Blumberg | 402/8 |
| 5,643,319 A | | 7/1997 | Green et al. | |
| 5,718,359 A | | 2/1998 | Palmer et al. | |
| 5,755,371 A | | 5/1998 | Huang | |
| 5,891,168 A | | 4/1999 | Thal | |
| 6,179,840 B1 | * | 1/2001 | Bowman | 606/916 |
| 6,190,401 B1 | | 2/2001 | Green et al. | |
| 6,200,330 B1 | * | 3/2001 | Benderev et al. | 606/232 |
| 6,387,113 B1 | * | 5/2002 | Hawkins et al. | 606/219 |
| 6,423,073 B2 | * | 7/2002 | Bowman | 606/104 |
| 6,485,504 B1 | * | 11/2002 | Johnson et al. | 606/216 |
| 6,551,343 B1 | | 4/2003 | Törmälä et al. | |
| 6,554,852 B1 | * | 4/2003 | Oberlander | 606/232 |
| 6,601,748 B1 | * | 8/2003 | Fung et al. | 227/176.1 |
| 6,610,079 B1 | | 8/2003 | Li et al. | |
| 6,652,563 B2 | * | 11/2003 | Dreyfuss | 606/232 |
| 6,726,705 B2 | * | 4/2004 | Peterson et al. | 606/216 |
| 6,733,506 B1 | * | 5/2004 | McDevitt et al. | 606/104 |
| 6,830,573 B2 | | 12/2004 | Strong et al. | |
| 6,991,643 B2 | | 1/2006 | Saadat | |
| 7,028,878 B2 | | 4/2006 | Bauer | |
| 7,033,379 B2 | | 4/2006 | Peterson | |
| 7,048,171 B2 | * | 5/2006 | Thornton et al. | 227/176.1 |
| 7,056,331 B2 | | 6/2006 | Kaplan et al. | |
| 7,104,999 B2 | * | 9/2006 | Overaker | 606/142 |
| 7,112,214 B2 | | 9/2006 | Peterson et al. | |
| 7,118,581 B2 | * | 10/2006 | Friden | 606/104 |
| D532,107 S | | 11/2006 | Peterson et al. | |
| 7,547,315 B2 | | 6/2009 | Peterson et al. | |
| 8,016,867 B2 | | 9/2011 | Bowman | |
| 8,105,342 B2 | | 1/2012 | Onuki et al. | |
| 2001/0027322 A1 | | 10/2001 | Bowman | |
| 2003/0167072 A1 | * | 9/2003 | Oberlander | 606/232 |
| 2005/0116008 A1 | * | 6/2005 | Thornton et al. | 227/176.1 |
| 2005/0149064 A1 | * | 7/2005 | Peterson et al. | 606/143 |
| 2005/0288689 A1 | | 12/2005 | Kammerer et al. | |
| 2006/0009792 A1 | | 1/2006 | Baker et al. | |
| 2006/0011693 A1 | * | 1/2006 | Wywialowski et al. | 227/109 |
| 2006/0097027 A1 | * | 5/2006 | Brown | 227/175.1 |
| 2006/0253131 A1 | | 11/2006 | Wolniewicz | |
| 2009/0206127 A1 | | 8/2009 | Danielson et al. | |
| 2012/0325889 A1 | | 12/2012 | Danielson et al. | |

OTHER PUBLICATIONS

International Preliminary Report on Patentability for corresponding international application No. PCT/US07/15418, issued Jan. 6, 2009, 4 pages.

International Search Report for corresponding international application No. PCT/US07/15418, mailed Sep. 8, 2008, six pages.

Extended European Search Report for Application No. 07810174.8, dated Dec. 21, 2012, 8 pages.

* cited by examiner

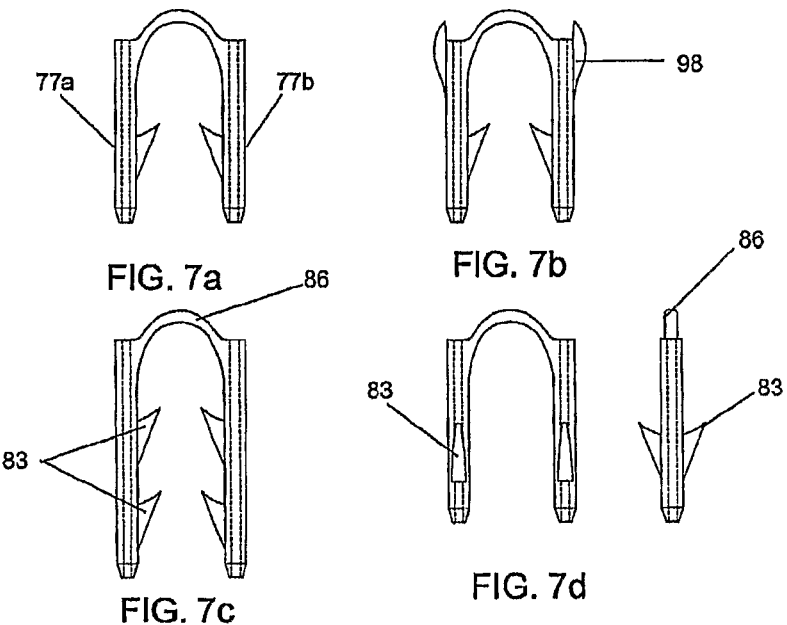
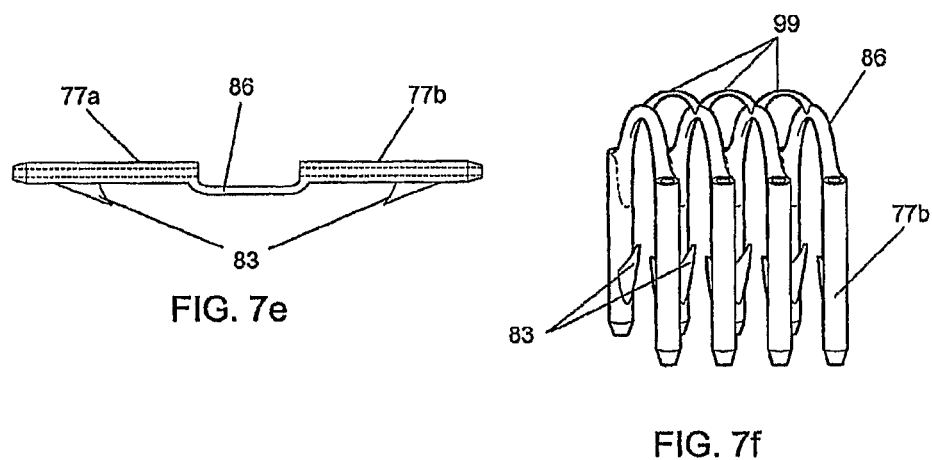
FIG. 7a  FIG. 7b  FIG. 7c  FIG. 7d  FIG. 7e  FIG. 7f

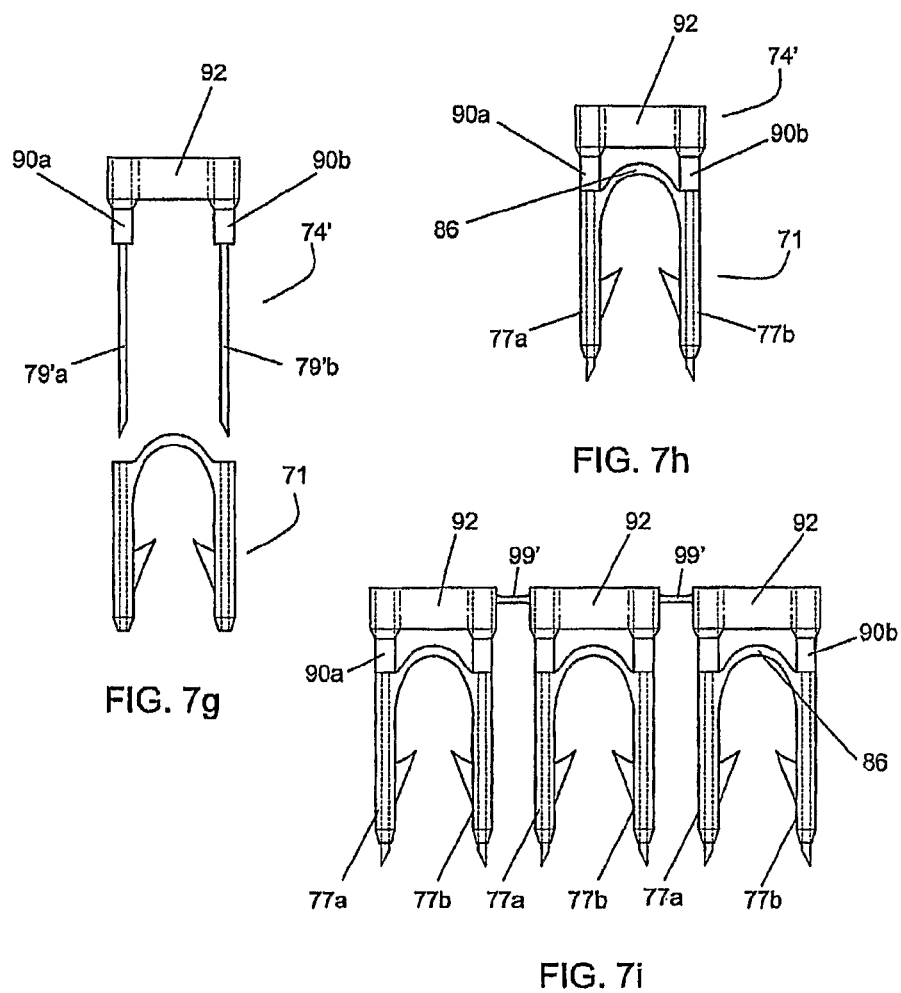

US 8,506,591 B2

TISSUE FASTENERS AND RELATED INSERTION DEVICES, MECHANISMS, AND METHODS

CROSS-REFERENCE TO RELATED APPLICATIONS

This is a U.S. National Phase of International Patent Application Number PCT/US2007/015418, filed Jun. 29, 2007. That international application claims the benefit of and priority to Provisional U.S. Patent Application Ser. No. 60/817,858, filed Jul. 1, 2006. The entirety of the contents of each of the international and provisional patent applications is incorporated herein by reference.

TECHNICAL FIELD

This invention relates to fasteners for apposing the two sides of an incision or cut in human skin and other tissue and, more particularly, to bioabsorbable fasteners and related insertion devices.

BACKGROUND INFORMATION

Sutures for closing incisions in human skin are well known. The sutures are applied by physicians using a needle to pull the suture material through the two sides of the incision. The suture material is tied which fastens or apposes the two sides to allow healing. The suture material may be non-absorbable such as silk, polyester, etc. or it may be formed from bioabsorbable materials such as polyglycolic acid polymers. Applying sutures in this way requires skill and dexterity. Also it exposes the operator to possible needle stick injury. For these reasons and because of the time that it takes to apply sutures, other fasteners have been developed, the most popular of these being referred to as staples.

Surgical staples are made of non-reactive metals and are strong enough to hold the tissues together once the ends of the staple have been bent inward. Although staples are faster and safer to apply than sutures, they have disadvantages. Because they penetrate the epidermis and remain exposed on the surface of the skin, they (i) present an opportunity for infection, (ii) the wound must be kept dry until the staples are removed (5-7 days), and (iii) the patient must return for removal which requires another device, is time consuming, inconvenient and can cause discomfort.

Recently staples have been made of bioabsorbable plastics so that they can be applied below the skin and will not require removal. To have sufficient strength to penetrate the skin and secure the tissue, the plastic typically must be much larger in cross section than an equivalent metal staple. For example, a staple wire with diameter of 0.65 mm in metal would need to have a diameter of 2.5 mm to have the same bending or buckling strength if made of plastic. Hence, the bioabsorbable staples tend to be bulky and to occupy significant volume within the wound. In addition, the means of applying the plastic staple may be complex.

U.S. Pat. No. 6,726,705 relates to a mechanical method and apparatus for fastening tissue.

SUMMARY OF THE INVENTION

There exists a need for a biodegradable or bioabsorbable fastener that can be easily deployed from above the incision or other wound and that can be used to close minimally invasive surgery incisions as short as 5 mm and that will hold the tissue apposed, lie below the surface of the skin, and occupy a small volume within the wound.

In one aspect, the invention generally relates to a tissue fastener comprising a bridge section and first and second leg sections. The bridge section includes a first portion and a second portion. The first leg section is integral with the bridge section and extends from the first portion of the bridge section. At least a portion of the first leg section defines a first lumen extending therethrough such that the first leg section is cannulated. The second leg section also is integral with the bridge section, and it extends from the second portion of the bridge section. At least a portion of the second leg section defines a second lumen extending therethrough such that the second leg section also is cannulated. The bridge section and the first and second leg sections comprise a single piece of material.

In accordance with this aspect of the invention, various embodiments are possible. For example, the single piece of material can be bioabsorbable, and the bioabsorbable material can be a polyglycolic acid polymer, a copolymer, or a blend of polymers. Also, each of the first and second leg sections can include at least one barb, and the at least one barb can be oriented in a direction away from the surface of tissue after the tissue fastener is inserted into the tissue. In general, the barbs are oriented to resist dislodgement from tissue after the tissue fastener is inserted into the tissue. In addition, the bridge section can be sufficiently flexible to allow the first and second leg sections to spread angularly after the tissue fastener is inserted into tissue. And, a portion of each of the first and second leg sections can be tapered. Also, the bridge section can include a frangible connector for releasably connecting the bridge section to another tissue fastener.

In another aspect, the invention generally involves a tissue fastening system comprising the tissue fastener described above and also an insertion device for deploying the tissue fastener into tissue.

In accordance with this other aspect of the invention, various embodiments also are possible. For example, the insertion device can be part of a larger insertion mechanism that an operator (such as a surgeon) manually operates to move indirectly the insertion device to deploy the tissue fastener from above the tissue in a generally perpendicular orientation in relation to the surface of the tissue. Also, the insertion device can include a first needle for insertion into the first lumen of the cannulated first leg section and a second needle for insertion into the second lumen of the cannulated second leg section, and these needles can be substantially parallel to each other.

In yet another aspect, the invention generally features a tissue fastening system comprising the above-described tissue fastener and an insertion mechanism for deploying the tissue fastener into tissue. The insertion mechanism includes an insertion device, and the insertion device is utilized to deploy the tissue fastener from above and generally perpendicular to the tissue.

In still another aspect, the invention generally involves a tissue fastening system comprising the above-described tissue fastener, an insertion device for deploying the tissue fastener into tissue, and compressing forceps that include first and second arms where each of the arms includes a surface for contacting the tissue. The first and second arms can include a pair of movable tissue compressing arms.

The present invention also generally relates to a cannulated fastener device made from bioabsorbable plastic materials. Accordingly, the bioabsorbable fastener comprises two legs cannulated to receive an insertion device (which can be at least partially metallic), each leg having at least one barb oriented to resist retraction of the fastener after deployment into tissue. The two legs are connected by a flexible bridge and initially oriented parallel to each other. The bridge may be formed from a bioabsorbable polymer that becomes flexible at body temperature and/or can be shaped in a manner, such as having a rectangular cross-section, which bends easily and allows the legs to spread angularly after insertion.

A fastener according to the invention is designed to hold the tissue in apposition while remaining totally below the surface of the skin. Accordingly, one preferred target area for each leg is the deep surface of the dermis between 1 and 4 mm, and preferably between 2 and 3 mm displaced from the cut surface in one embodiment. After the opposing walls of the wound (or other tissue slit or opening) are pulled apart and everted to expose the inner surface of each of the walls upward, needles or other sharp injection members of the insertion device penetrate the deep surface of the everted dermis and drive the fastener and its barbs into the body of the dermal tissue from above the surface of the skin. After insertion of the bioabsorbable fastener, the delivering needles are withdrawn, leaving the fastener within the tissue and the tissue is released to allow the skin to relax as the legs of the embedded fastener open outwardly. The resulting final orientation of the embedded fastener brings the barbs into tension when the two sides of the tissue are apposed and slightly everted with the fastener resting completely below the surface of the skin.

A fastener according to the invention is designed to occupy a small volume within the wound to promote wound healing. Accordingly, the legs of the bioabsorbable fastener are cannulated with very thin side walls having a radial thickness between 0.1 and 0.5 mm, for example, and preferably between 0.2 and 0.3 mm in one embodiment. The thin walls of the legs are tapered inwardly at their distal ends so that they reduce the penetrating force needed to insert them into the tissue. Strength to penetrate human tissue is provided by an insertion device, which has dual metallic needles in one embodiment, dimensioned so that they slide into the two legs of the fastener and exit the tapered ends of each leg. The dual needles are sharpened at their distal ends thus providing a sharp point for entry into the tissue to be apposed.

A fastener made according to the present invention holds the two apposing tissues together by tension forces between the barbs at the ends of each leg. A bioabsorbable material, such as a polyglycolic acid polymer, a copolymer, or a blend of polymers, is chosen to have mechanical properties such that each cannulated leg has a tensile breaking strength of 2.5 pounds or greater in one embodiment. One bioabsorbable material is polyglycolide, which is also known as polyglycolic acid or (PGA), and it has a glass transition temperature of 35-40° C., which is sufficiently low to allow the fastener, especially the bridge structure connecting the two legs, to become flexible at body temperature. Since the present fasteners operate in tension, while other staples operate by their structural strength, compressive strength, or resistance to deforming, fasteners according to the present invention do not need to be as massive, thus reducing the volume of foreign material in the wound.

Fasteners according to the invention are designed to be deployed from above the skin. Accordingly, one embodiment of the present invention provides specially adapted compressing forceps or presser feet that are used in conjunction with tissue manipulators to evert the tissues to be apposed and thereby turn them upwards and also to compress them to a predetermined dimension suitable for accepting the fastener. The fastener, mounted on the insertion device, then may be manually driven into the tissue in the predetermined space between the compressing forceps. In an alternate embodiment, the compressing forceps can be used in conjunction with a stapler-like device to deploy the fasteners. The stapler-like device may be manually positioned with respect to the compressing forceps using indexing pins or other features suitable for mechanically referencing one part to another.

Fasteners according to the invention are designed to be deployed easily and reproducibly without requiring special dexterity. An insertion mechanism may be used (in conjunction, for example, with tissue manipulators) to provide a way to reproducibly position the surfaces of the dermal layer and to deploy the fastener. The insertion mechanism desireably is able to carry multiple fasteners of the present invention, and comprises a means for loading the fasteners one at a time onto the insertion device by passing the sharpened needles of the insertion device through the legs of the fastener. Alternatively, the insertion mechanism can carry a cartridge of insertion devices each pre-loaded with a bioabsorbable fastener of the present invention, and means for moving the insertion devices one at a time into the translating mechanism to drive into the tissue and then retract the insertion device thereby leaving the fastener in place. The insertion mechanism has two features (indentations or slots) into which two manipulators are positioned, each having pinched one side of the tissue to be apposed. Tissue compressing arms, located on either side of the insertion mechanism, move in unison when the user presses an actuating lever. The tissue compressing arms descend, opposing the tissue below the points held in place by the tissue manipulators, and positions the two sides of the tissue against one another. The insertion mechanism further comprises an actuation arm attached to the insertion device which allows only vertical translation synchronized to deploy the insertion device carrying one of the fasteners after the tissue is positioned. This vertical translation may be driven by electromotive, spring, or manual force through coupling arms, or other means known in the art for driving staples. The final downward position may be constrained by a mechanical stop adjusted to deploy the fastener to a desired depth in the tissue. In an alternate embodiment, the final downward position is determined by a limiting spring, which is chosen to compress significantly only when a force comparable to the maximum force to be applied to the insertion device to seat the fastener fully within the everted tissue is applied.

Needles of the insertion device do not need to be exposed until the deployment mechanism is activated, thus the risk of needle sticks to the operator is minimized. At the completion of the inserting actions accomplished by any of the above or other means, the insertion device is retracted leaving the fastener in place in the tissue. Further retraction of the actuation mechanism allows the insertion mechanism to be withdrawn and the tissue compressing arms to reopen. As a final step of a method to deploy the fastener, the user urges the two sides of the tissue that have been held with the tissue manipulators toward the line of apposition until the cut surfaces come into contact with one another, and then releases the epidermis.

Indications for the bioabsorbable fastener of the present invention include minimally invasive surgical skin wound closure as well as longer skin wound closure (both surgical and accidental). Also, approximating other tissues, such as intestines, arteries and veins, or any soft tissue apposition in an everted or inverted orientation such as anastamoses, are procedures that would benefit from the present invention. While the present invention is described utilizing bioabsorbable materials, it will be appreciated that in some circumstances many of the benefits of the fastener can be achieved using non-bioabsorbable materials.

Accordingly, an aspect of the invention involves a fastener for use in apposing body tissues, said fastener being fabricated from bioabsorbable material such as a polyglycolic acid, a copolymer, or a blend of polymers. The fastener is formed to have two legs, each leg having an inwardly tapered distal end and barbs oriented to resist dislodgement of the fastener after insertion into tissue. The two legs are connected by a flexible bridge at their proximal end and cannulated to receive an insertion device, which extends through the legs and exits the distal end exposing a sharp point to facilitate insertion of the fastener into tissue.

Another aspect of the invention relates to a method for apposing the tissues in closing a surgical incision or wound utilizing a bioabsorbable fastener of the present invention, tissue manipulators, and an insertion device. The method comprises use of tissue manipulators to pull upwards and index the two sides to be apposed with respect to compressing forceps, such procedure being adapted to roll the surfaces of the dermis from a horizontal to a vertical orientation while compressing the tissue together. The two sides of the incision or wound are held in this upward facing orientation while the bioabsorbable fastener is inserted from above.

Still another aspect of invention comprises an insertion mechanism able to carry multiple fasteners of the present invention, at least one insertion device having two sharpened needles inserted into the cannulated legs of the fastener to facilitate penetration of the tissue, mechanical means to reference the two sides of the tissue to be apposed, to compress and hold the tissue in a favorable orientation for receiving the fastener, and a translating mechanism to drive and then retract the at least one insertion device into the tissue thereby leaving the fastener in place.

Disclosed and contemplated embodiments of tissue fasteners, insertion mechanisms, insertion devices, and methods for closing a wound (whether created surgically or otherwise) with the fastener, in accordance with the invention, are different in a variety of ways than known surgical staples and related stapler devices. For example, embodiments of tissue fasteners according to the invention are structurally distinct from known staples. Also, as another example, the inventive fasteners are deployed in a distinct way. As yet another example, fasteners according to the invention, once deployed into the body hold wounds together by tension.

Other aspects, objects, and advantages of the invention are included herein even if not expressly called out. The disclosed embodiments are exemplary and not limiting.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which:

FIGS. 7a through 7e show alternate embodiments of the bioabsorbable fastener;

FIG. 7f shows a plurality of fasteners molded into an assembly in which linked components interconnect the bridges of the fasteners;

FIGS. 7g, 7h, and 7i show assemblies of fasteners and insertion devices created by an insert molding process;

FIG. 13b shows a top view of the fastener of FIG. 13a;

DESCRIPTION

Figure 1:
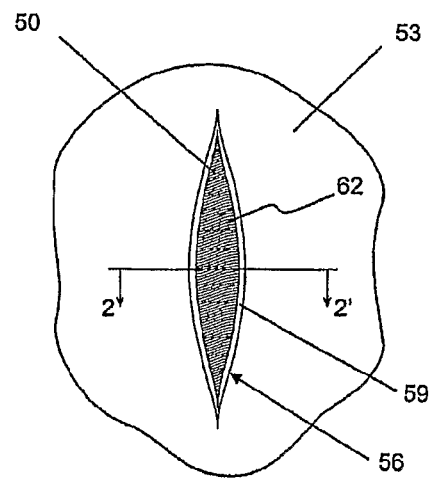
FIG. 1 shows a typical incision in the skin of the type that may be closed using the present invention.

With reference to FIG. 1, an opening 50 in the skin 53 is shown such as may be caused by an incision or wound. For purposes of this description, the "upward" or vertical direction is that direction generally perpendicular to the surface of the skin 53, even if that surface is curved or facing in another direction. Human skin is comprised of layers that are indicated in FIG. 1 and seen in FIG. 2 which is a cross-section taken along line 2-2'. The outermost layer, the epidermis 56 consists of mostly dead cells. Below this is found the dermal layer 59 that is a thin layer of strong living tissue and then the subcutaneous layer 62. While the present invention will be described with reference to openings in human skin 53, it will be understood that approximating other tissues such as intestines, arteries and veins, or any soft tissue apposition in an everted or inverted orientation such as anastamoses, can benefit from the present invention.

Figure 2:
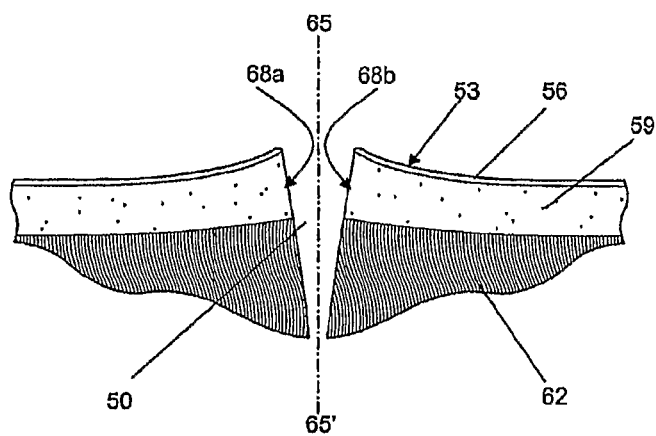
FIG. 2 is a cross section of incision shown in FIG. 1 taken along the section 2-2'.

In FIG. 2, the line of apposition 65 represents a vertical plane that runs longitudinally bisecting the opening 50 in the skin 53. To facilitate the healing process, the surfaces 68a and 68b of the living dermal layer must be brought together and held in close contact for several days.

Figures 3A, 3B:
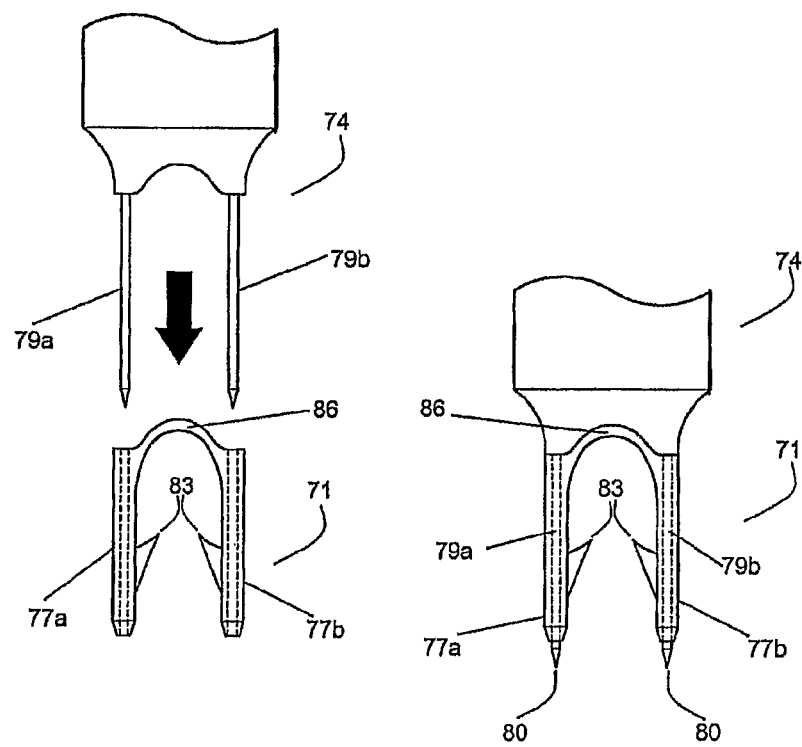
FIG. 3a shows the insertion device positioned to be inserted into the legs of the bioabsorbable fastener of the present invention.
FIG. 3b shows the bioabsorbable fastener of the present invention positioned on the insertion device ready to be deployed.

In FIG. 3a and FIG. 3b, the fastener 71 of the present invention is positioned in relation to the driving end of an insertion device 74. The fastener 71 is mounted onto the insertion device 74 for purposes of deploying the fastener into tissue. The fastener 71 is made from bioabsorbable plastic materials such as polyglycolides and comprises two legs 77a, 77b cannulated to receive the insertion needles 79a, 79b of the insertion device 74. In FIG. 3a, the insertion device 74 is shown aligned for insertion into the fastener 71, while FIG. 3b shows the two components fully assembled, as would be the case prior to deployment into tissue. The needles 79a, 79b of the insertion device 74, when fully inserted in the legs 77a, 77b as shown in FIG. 3b, extend a small distance beyond the distal end of legs 77a, 77b to expose sharp ends 80. The sharp ends 80 facilitate penetration into tissue. The sharp ends 80 can be, for example, tapered similar to a typical pencil point, as shown in FIG. 3b and other figures. If the sharp ends 80 are tapered, each of them has a centered point, as would a sharpened pencil. The sharp ends 80 instead can be, for example, beveled as shown in FIGS. 7g-7i. Each leg 77a or 77b of the fastener 71 has at least one barb 83 oriented to resist retraction of the fastener 71 after deployment into tissue. The two legs 77a, 77b are connected at the proximal end by a flexible bridge 86.

Figure 4A:
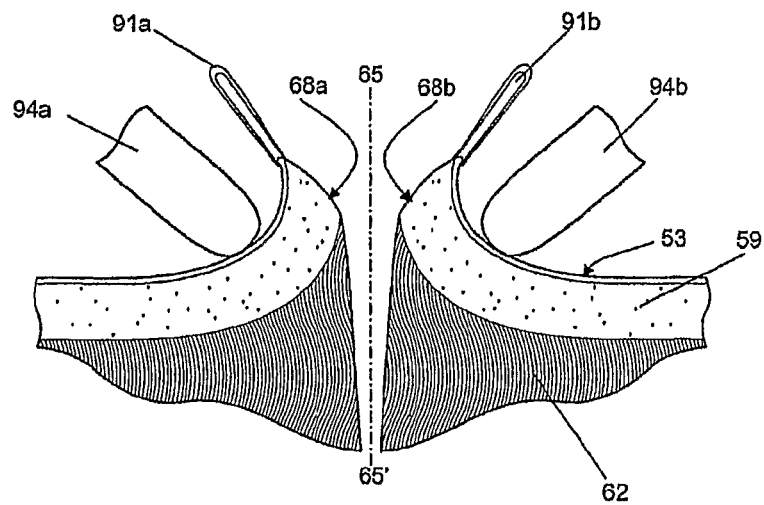
FIG. 4a is a cross section of the skin tissue of FIG. 2 raised by pulling upwards using tissue manipulators.
Figure 4B:
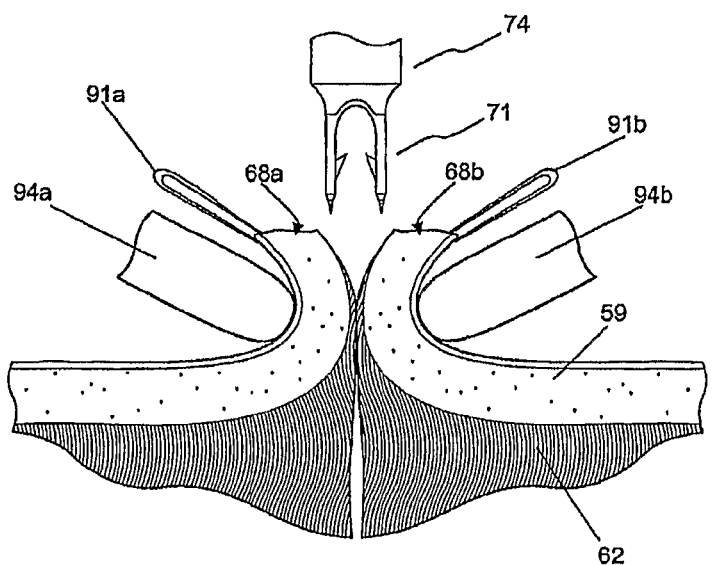
FIG. 4b is a cross section similar to FIG. 4a showing the tissue further oriented for receiving the fastener of the present invention and the insertion device with a bioabsorbable fastener ready to be deployed.

FIG. 4a shows the skin 53 being pulled upward by tissue manipulators 91a, 91b while being urged toward the line of apposition 65 by arms 94a, 94b. Continued pulling by tissue manipulators 91a, 91b as shown in FIG. 4b and urging by arms 94a, 94b causes the surfaces 68a, 68b of the dermal layer to move from a generally vertical orientation facing each other, to a generally horizontal one facing upward pulling it away from the subdermal tissue and exposing the underside of the dermal layer. In FIG. 4b, the insertion device 74 carrying the fastener 71 is shown in the correct orientation prior to inserting the fastener 71 into the tissue.

Figure 5A:
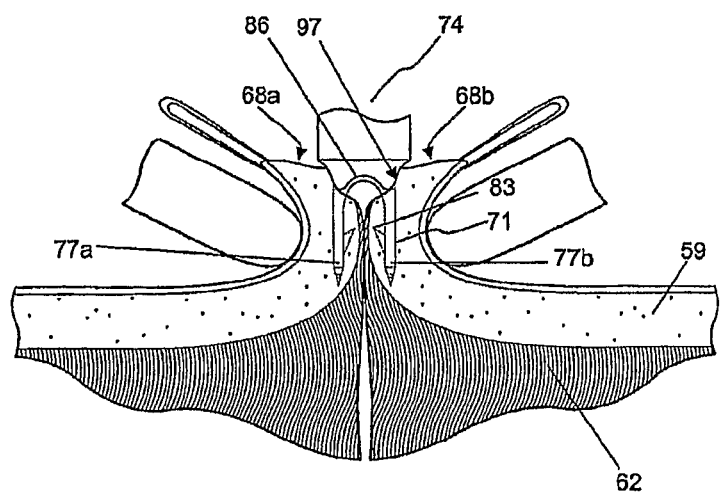
FIG. 5a shows a cross section of skin tissue similar to FIG. 4b with the bioabsorbable fastener and insertion device deployed.

FIG. 5a shows the insertion device 74 with fastener 71 after insertion showing the entry point for the legs 77a, 77b into the under side of the dermal layer 59. The displacement 97 indicated for leg 77b (and similar for leg 77a) is the distance along the underside of the dermal layer 59 from the cut surface 68b to the insertion point for leg 77b. This displacement 97 of the insertion point is approximately half the length of the bridge 86 where it connects the two legs 77a and 77b. We have found that this insertion technique allows the barbs 83 to engage the tissue at a depth sufficiently far from the surfaces 68a, 68b so that the bridge 86 can provide a tension holding the tissues together after the insertion device 74 is removed from the fastener 71 as shown in FIG. 5b.

Figure 5B:
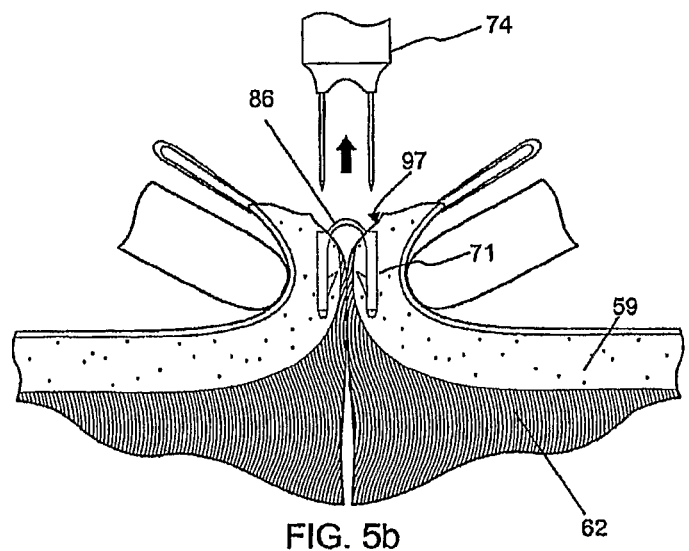
FIG. 5b shows the cross section of skin tissue of FIG. 5a after the insertion device has been removed.
Figure 6A:
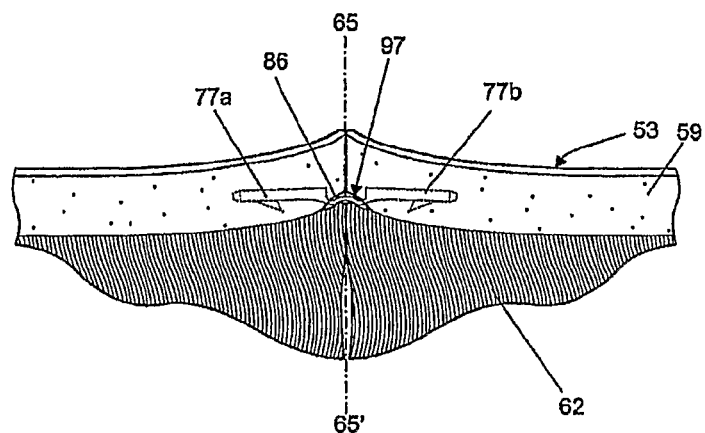
FIGS. 6a and 6b show the cross section of skin tissue of FIG. 5b after the tissue manipulator has been removed and the bridge connecting the legs of the bioabsorbable fastener has relaxed, for two possible embodiments of the bioabsorbable fastener.

FIG. 6 shows the tissues of FIG. 5b after the tissue manipulators 91a, 91b and arms 94a, 94b have been removed. The flexible bridge 86 bends easily and allows the legs 77a, 77b to spread angularly after the insertion device 74 is removed. A small amount of curvature may remain in the bridge 86, as it is desirable that the tissue be slightly everted where it meets along the line of apposition 65.

Figure 6B:
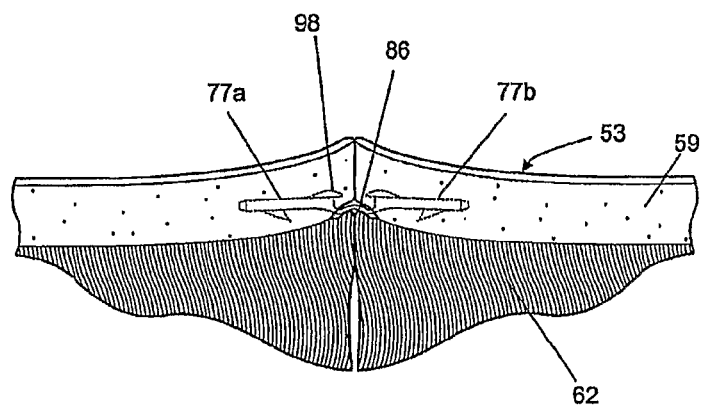

FIGS. 7a through 7e show alternate embodiments of the fastener 71 of the present invention differing principally in the position and number of barbs 83. The barbs may further lie in any plane that passes through the axis of the leg, either to facilitate manufacturing (e.g. using injection molding tooling) or to enhance the fastener's retention strength in tissue. However, it is desirable that no barb should be placed such that its pointed element, once the fastener is in place, is directed upwards towards the skin surface 53. The fastener in FIG. 7b adds axially directed barbs 98 at the top of each leg that can supplement the retention strength of the other barbs 83 when they are engaged as shown in FIG. 6b.

While the present description shows the fasteners individually, it will be understood that they may be placed in an assembly containing a plurality of fasteners held in relation to one another by a cartridge means or molded in such an assembly with inter connecting frangible plastic components 99, as shown in FIG. 7f. While the inter-connecting components 99 are shown for only one of the alternate embodiments it will be understood that components 99 can be added to other embodiments of FIGS. 7a to 7e.

To facilitate molding of the fasteners of the present invention either singly or in multiples, the legs 77a, 77b may be oriented in the open position similar to that shown in FIG. 7e with the bridge 86 straightened and subsequently bent to the configuration as shown in FIG. 7a prior to deployment.

In one embodiment, fasteners 71 can be made using a manufacturing process known as insert molding, as shown in FIGS. 7g through 7i. Referring to those figures, the insertion device 74' is fabricated prior to molding fastener 71. Needles 79'a and 79'b are installed in cylindrical shoulders 90a and 90b respectively which are part of yoke 92. Insertion device 74' is inserted into a molding cavity in an injection molding process, and the bioabsorbable polymer is injected around it to form fastener 71. FIG. 7h shows the combination of insertion device 79' and fastener 71 as molded by this process. FIG. 7i shows how the insert molding process described above can be used in a multi-cavity tool to yield multiple fasteners each connected to another by frangible components 99'.

Figure 8:
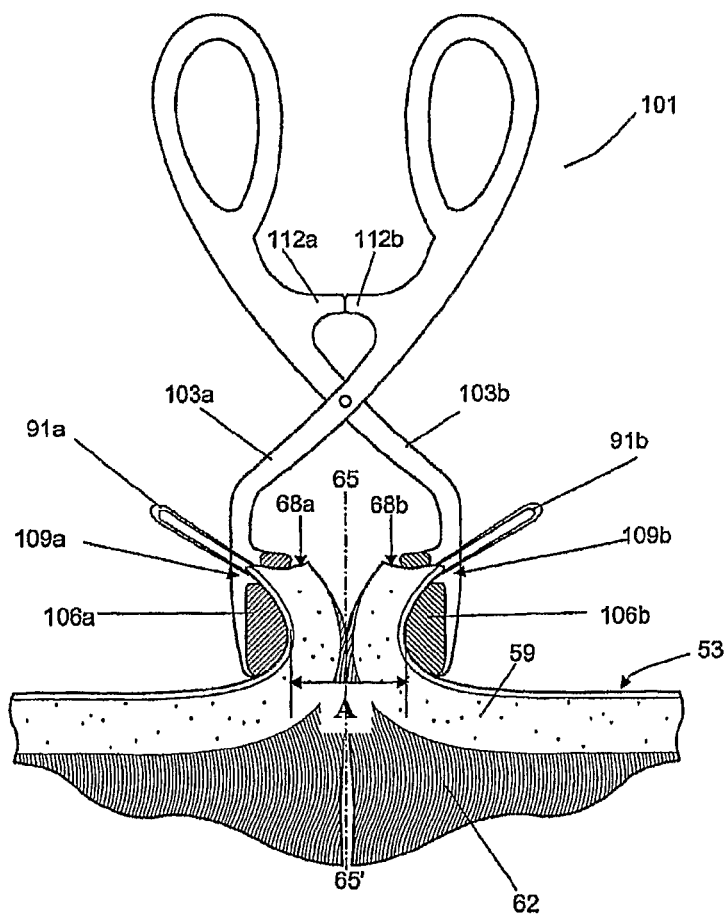
FIG. 8 shows a cross section of skin tissue similar to FIG. 5 with a specially adapted compressing forceps compressing the dermal tissues to be apposed.

FIG. 8 shows compressing forceps 101 that facilitate insertion of the bioabsorbable fastener of the present invention. The compressing forceps 101 have at the distal ends of each arm 103a, 103b, half-cylinder components 106a, 106b with features 109a, 109b (indentations or slots) at the top of the half-cylinder components 106a, 106b into which tissue manipulators 91a, 91b can be positioned. The user places the compressing forceps 101 so that each cylindrical component 106a, 106b presses against the skin 53 on either side of the line of apposition 65 with the axes of the cylinders parallel to incision or wound. Tissue manipulators 91a, 91b are used to pinch each side of the tissue to be apposed and pull it upwards indexing the tips of the manipulators in the features 109a, 109b at the top of the cylindrical component. The compressing forceps 101 are then squeezed until stopping elements 112a, 112b in the forceps meet to restrict further compression. The stopping elements 112a, 112b are designed to allow the tissues to be compressed leaving a predetermined distance of 4-8 mm separating the inner surfaces of the cylindrical components (dimension A in FIG. 8). This configuration assures that the cut surfaces 68a, 68b of the dermal layer are displaced away from the insertion device exposing the underside of the dermal layer and orienting it upwards to accept the fastener from above. The user deploys the fastener using the insertion device by penetrating the compressed dermal tissue between the two cylindrical components 106a, 106b. The compressing forceps 101 may also have indexing means to align an insertion device (not shown) so that it penetrates the underside of the dermal tissue equally spaced between the cylindrical components 106a, 106b.

FIGS. 9a-9d show an insertion mechanism 200 which provides a means for deploying the fastener 71 from above the skin 53. An alternate embodiment of the fastener 71, described above in FIG. 7b, is depicted being used with the insertion mechanism 200. Accordingly, one method uses an insertion mechanism 200 in conjunction with tissue manipulators 91a, 91b, to provide a means to coordinate the relative positions of the driving head of the insertion device 74, the tissue compressing arms 203a, 203b and the dermal layer. The tissue manipulators 91a, 91b are manually used to pinch the epidermis 56 and pull upwards on the two sides of the incision. The distal ends of the tissue manipulators 91a, 91b are then positioned in index cavities 206a, 206b which positions the cut surfaces 68a, 68b of the dermal layer away for the point of penetration on either side of the line of apposition 65. The tissue compressing arms 203a, 203b are movably attached to the insertion mechanism 200 as for example, with pivoting elements 209a, 209b. The tissue compressing arms 203a, 203b, located on either side of the insertion mechanism 200, move in unison when the user presses an actuating lever (not shown). At the distal ends of the tissue compressing arms 203a, 203b there are cylindrical elements 213a, 213b which contact the tissue below the points held in place by the tissue manipulators 91a, 91b, and compress the two sides of the tissue against one another. The insertion mechanism 200 further comprises an actuation arm 216 attached to the insertion device 74 which allows only vertical translation synchronized to deploy the insertion device 74 carrying one of the fasteners 71 after the tissue is compressed. This vertical translation may be driven by electromotive, spring, or manual force through coupling arms, or other means known in the art for driving staples. The final downward position may be constrained by a mechanical stop (not shown) adjusted to deploy the fastener to a desired depth in the tissue. In an alternate embodiment, the final downward position is determined by a limiting spring 219, which is chosen to compress significantly only when a force comparable to the maximum force to be applied to the insertion device to seat the fastener fully within the everted tissue is applied. If the motive force for the actuation arm 216 is manual force the limiting spring 219 can provide force feedback to the user without appreciably advancing the fastener further into the tissue. This adds a degree of compliance to the mechanism making the exact vertical position of the surfaces 68a, 68b of the dermis less critical than with a rigid mechanism. In addition, the likelihood of tissue tearing as a result of excessive force applied to the actuation arm 216 is reduced so long as the user remains sensitive to the maximum appropriate force to be applied.

Figure 9A:
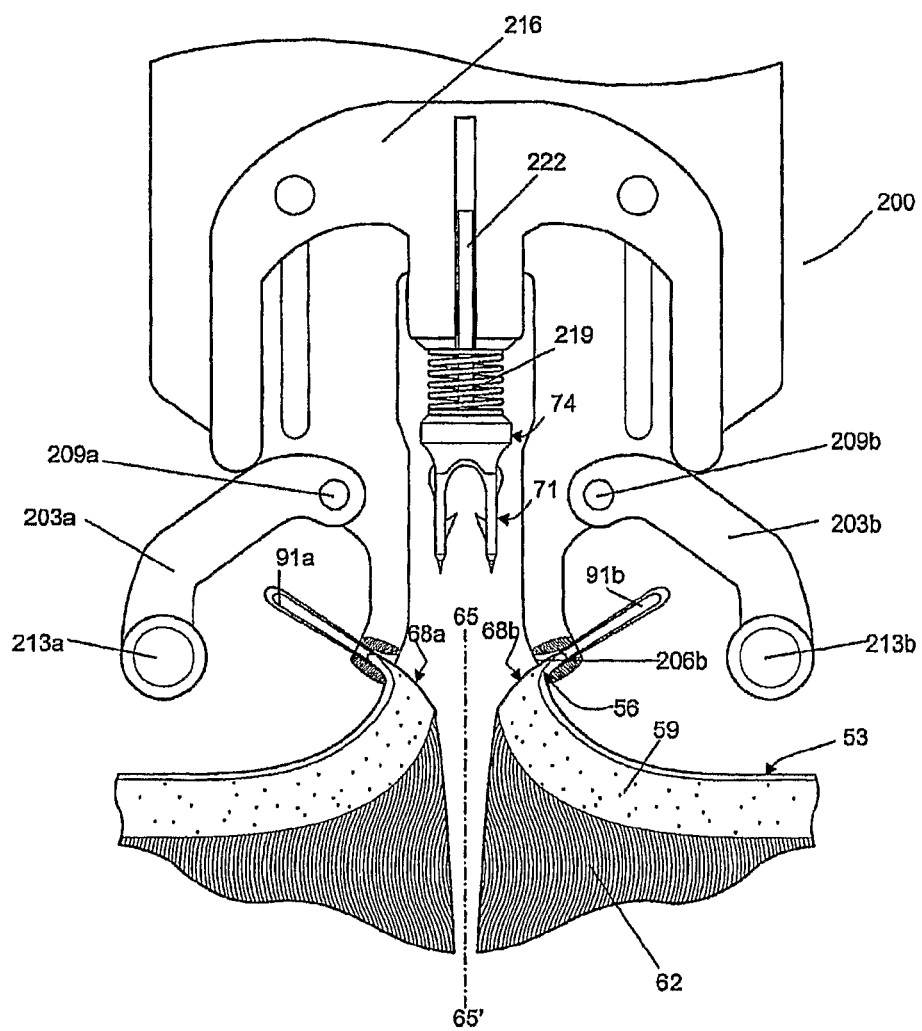
FIGS. 9a through 9d show the process illustrated in FIGS. 4 and 5 implemented with the aid of a mechanism that coordinates the several steps.

The different steps of a method of the present invention are shown in FIG. 9a-9d. In FIG. 9a, tissue manipulators 91a, 91b have pinched the epidermis 56 on either side of the wound to be apposed and the insertion mechanism 200 has been brought into place. The tissue manipulators 91a, 91b have been located to index cavities 206a, 206b provided on the insertion mechanism for this purpose. A fastener 71 has been mounted on the insertion device 74, which is in turn mounted to the actuation arm 216 by means of a shaft 222 that allows only vertical translation.

Figure 9B:
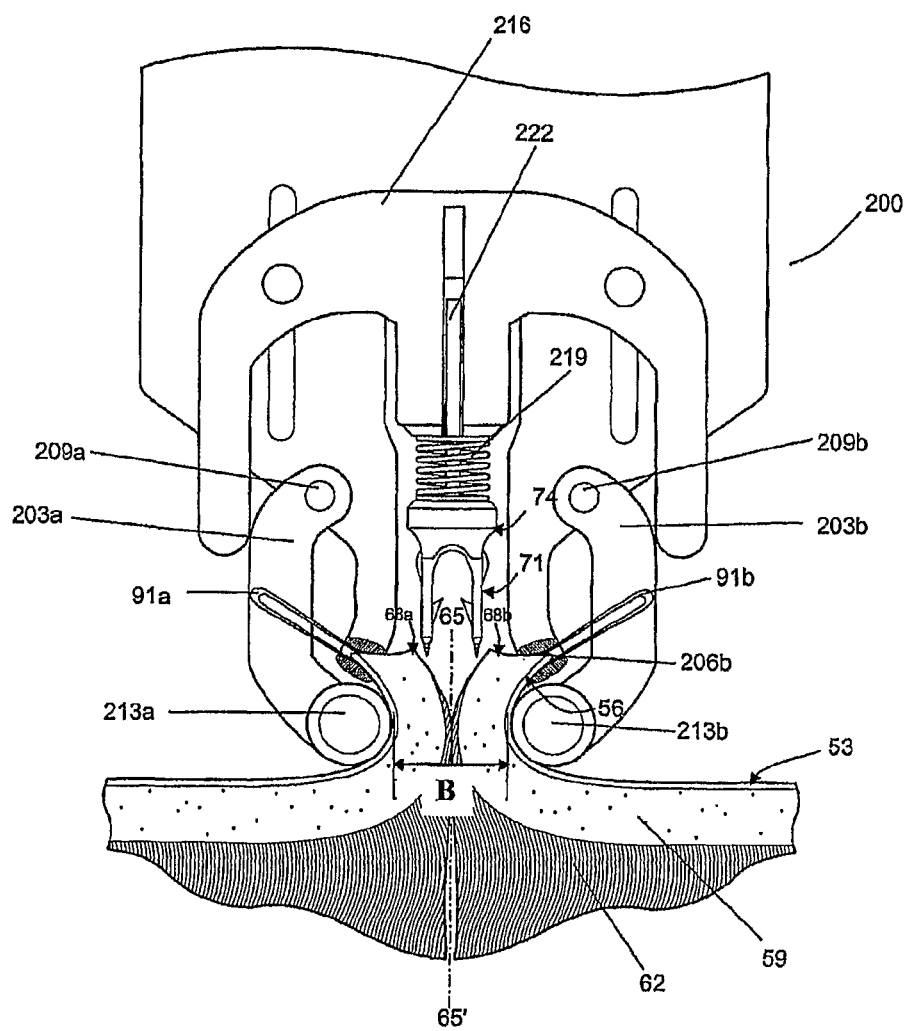

In FIG. 9b, the actuating arm 216 of the mechanism has started to descend, forcing tissue compressing arms 203a, 203b against the edges of epidermis 56 held by the tissue manipulators 91a, 91b. Movement of the tissue compressing arms 203a, 203b is limited by the engagement of the actuating arm 216 such that the cylindrical elements 213a, 213b remain separated a predetermined distance between 4 mm and 8 mm as indicated by dimension "B". The fastener 71 is shown ready to descend with the insertion device 74 driven by the actuation arm 216 towards the underside of the dermal layer of the wound.

Figure 9C:
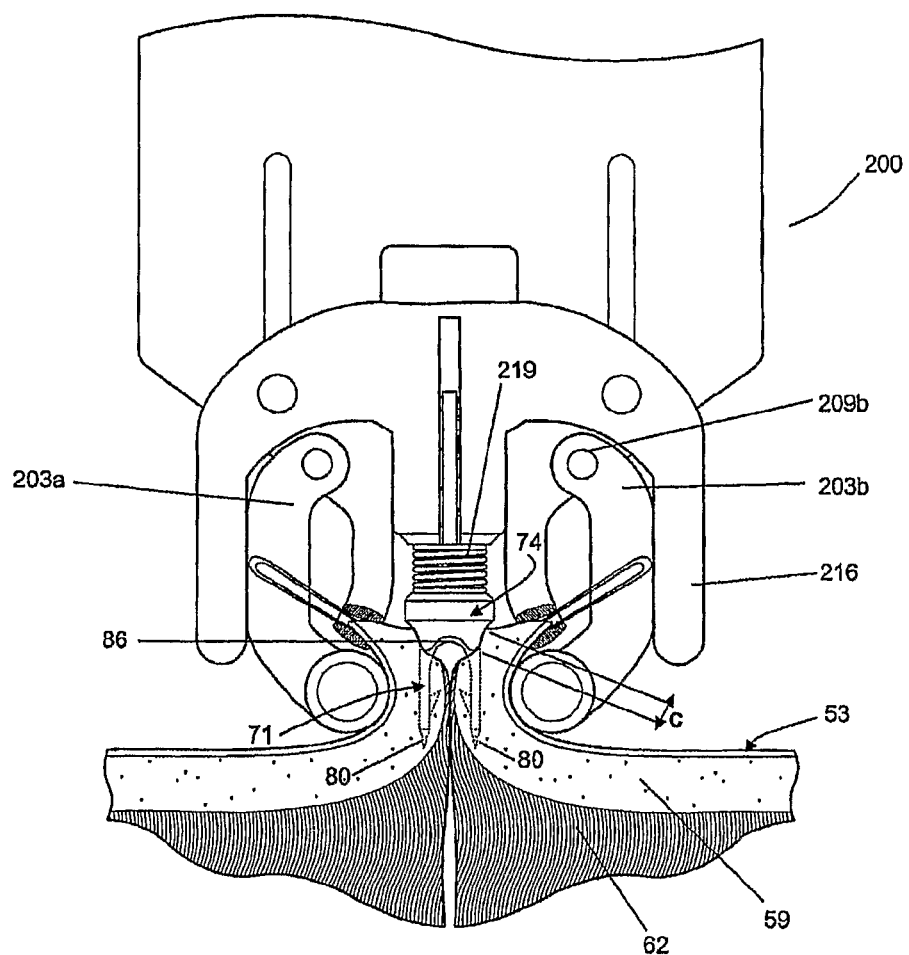

In FIG. 9c, the actuating arm 216 of the insertion mechanism 200 has descended further than in FIG. 9b, maintaining the position of the tissue compressing arms 203a, 203b while inserting the fastener 71 into the tissue with the aid of the sharp ends 80 of the insertion device 74. (As indicated previously, the sharp ends 80 can be tapered as shown in FIG. 3b or beveled as shown in FIGS. 7g-7i, to give just two examples of the possible shapes of the sharp ends 80.) The limiting spring 219 is compressing, which builds up the force feedback on the user who is providing the motivating force on the actuation arm without appreciably advancing the fastener further into the tissue. The fastener 71 is desireably inserted at a point that is displaced from the edge of the cut surfaces 68a, 68b by a distance C that is approximately half the length of the bridge 86 of the fastener 71.

Figure 9D:
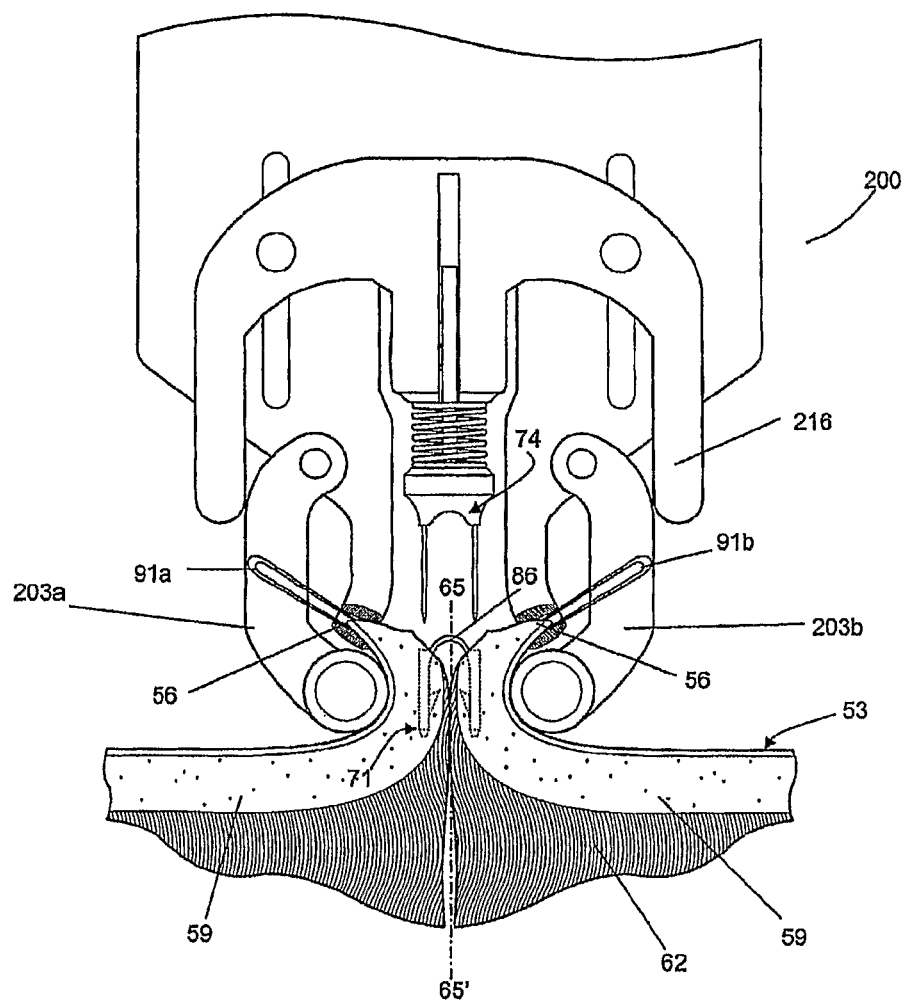

In FIG. 9d, the actuation arm 216 is shown in a partially retracted position leaving the fastener 71 in place in the dermal layer 59. Remaining steps, not illustrated, include the further retraction of the actuation arm 216, allowing the tissue compressing arms 203a, 203b to reopen, and the insertion mechanism 200 to be withdrawn while the tissue manipulators 91a, 91b momentarily retain the edges of the epidermis 56. As a final step the user brings the tissue manipulators 91a and 91b together along the line of apposition thereby pulling the two sides of the dermal layer 59 until the surfaces 68a, 68b of the dermal layer touch one another. Since the points of insertion are a distance C from each of the surfaces 68a, 68b, and the distance of twice C is approximately equal to the length of the bridge 86, the bridge straightens and comes into tension at the point where the surfaces 68a, 68b touch.

Figure 10:
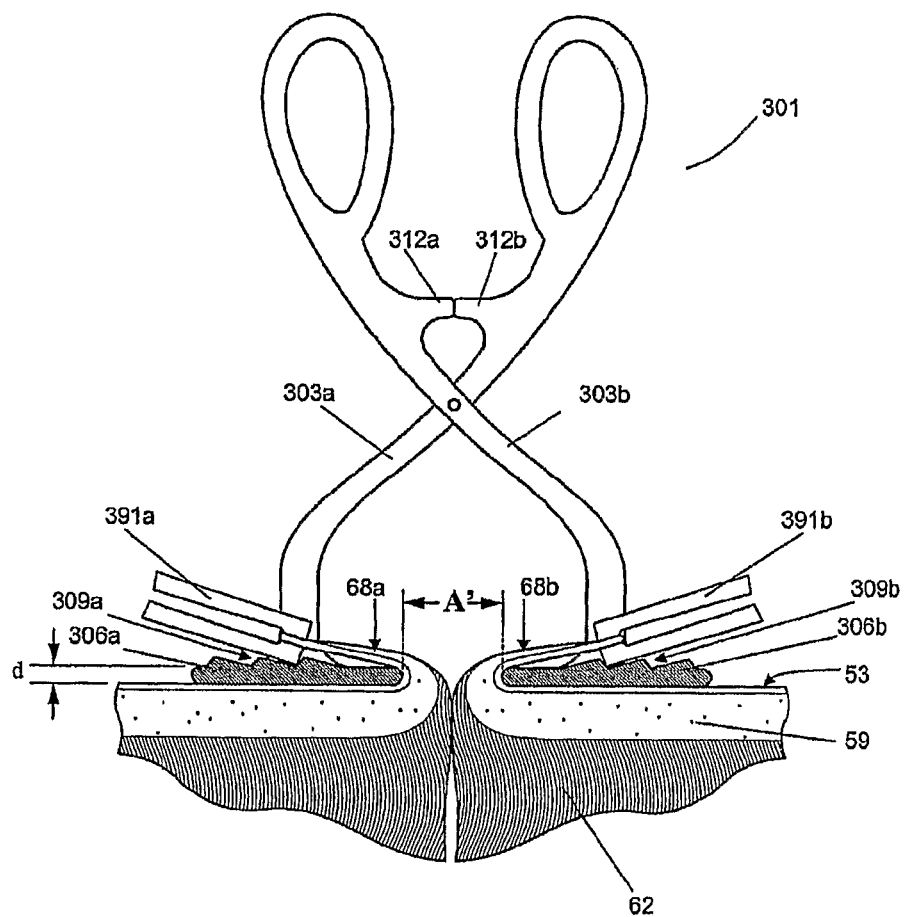
FIG. 10 shows a modification of the arrangement depicted in FIG. 8, now equipped with presser feet for approximating the cut surfaces of the tissue to be repaired.

In an alternative embodiment, FIG. 10 shows compressing forceps 301 having tissue contacting members 306a and 306b that are referred to herein as presser feet and which are shown in FIG. 10 in cross section. The presser feet 306a and 306b have a lower vertical profile than the half-cylinder components 106a and 106b of compressing forceps 101 of FIG. 8, with that height or profile of the presser feet 306a, 306b shown in FIG. 10 as "d" where "d" can be, for example, about 1.0 mm. This lower profile allows the cut surfaces 68a and 68b of the skin tissue to be everted and reflected over the presser feet 306a and 306b at a more acute angle than achievable with the arrangements of FIGS. 4, 5, 8, and 9. Reflecting the cut surfaces 68a and 68b at a more acute angle exposes the subcutaneous layer 62 of the dermis 59, permitting the insertion device 74 to insert the fastener 71 perpendicularly with respect to the plane of the skin surface 53 through the dermis 59 and into the subcutaneous layer 62.

The presser feet 306a and 306b can include surface features 309a and 309b for engaging the ends of tissue manipulators 391a and 391b. The surface features 309a and 309b can be notches or ridges, for example. By engaging the ends of tissue manipulators 391a and 391b, the surface features 309a and 309b help to stabilize the manipulators 391a and 391b in a fixed position once the cut surfaces 68a and 68b of the skin tissue have been elevated and reflected over the presser feet 306a and 306b to the extent desired. The presser feet 306a and 306b can be made of any sterilizable metal (such as stainless steel), sterilizable or single use plastic, or other material suitable for use in surgical instruments. They can be formed integrally with the arms 303a and 303b of the compressing forceps 301, or they can be attached by means of weld joints, screws, adhesive, and/or snap-fitting connecting members.

Figure 12A:
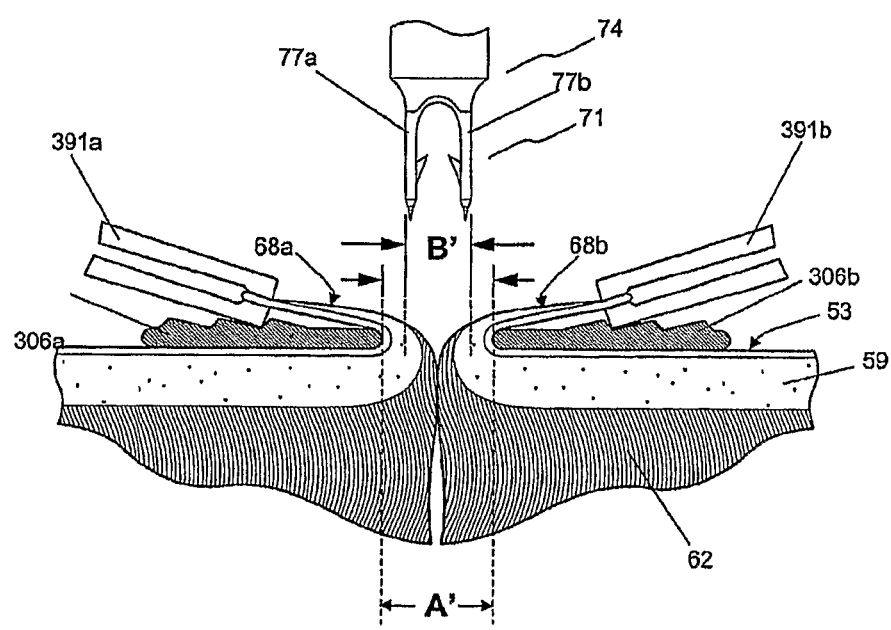
FIG. 12a shows a cross section of skin tissue as in FIG. 2 in which the cut surfaces of the tissue are raised and reflected over the presser feet by tissue manipulators, orienting the cut surfaces for receiving the bioabsorbable fastener, shown mounted on an insertion device.
Figure 12B:
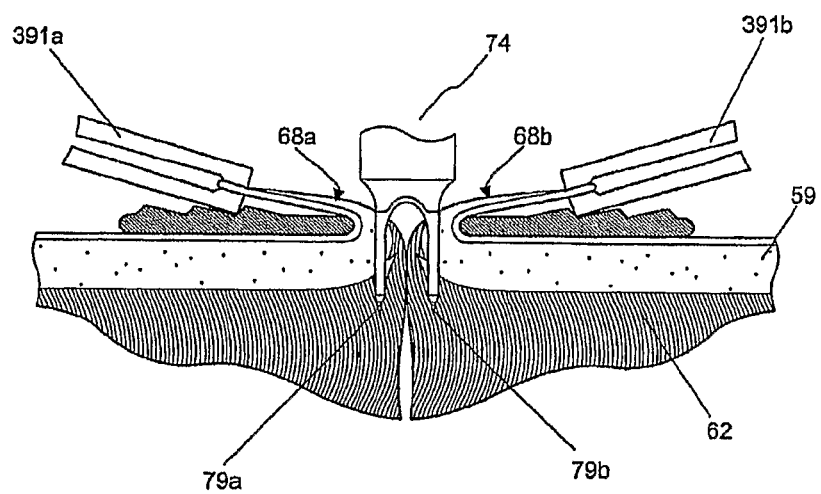
FIG. 12b shows the cross section of skin tissue as in FIG. 12a, with the bioabsorbable fastener and insertion device deployed and penetrating through the dermal layer.

The presser feet 306a and 306b can be brought into apposition by squeezing the compressing forceps 301 until the stopping elements 312a and 312b make contact. As shown in FIG. 10, a pre-determined gap A' remains between the opposing presser feet 306a and 306b when stopping element 312a makes contact with stopping element 312b. This gap A' is designed to bring the cut surfaces 68a and 68b together to the extent necessary to align fastener leg 77a with cut surface 68a, and fastener leg 77b with cut surface 68b, as shown in FIG. 12a. Gap A' is larger than fastener width B' by about 1.0 mm to ensure that fastener legs 77a and 77b reliably penetrate through the dermis 59 and partially into the subcutaneous tissue 62, as shown in FIG. 12b. For an embodiment with fastener width B' of 4.0 mm, the gap A' can be in the range of about 4.05 mm to about 4.15 mm.

Figure 12C:
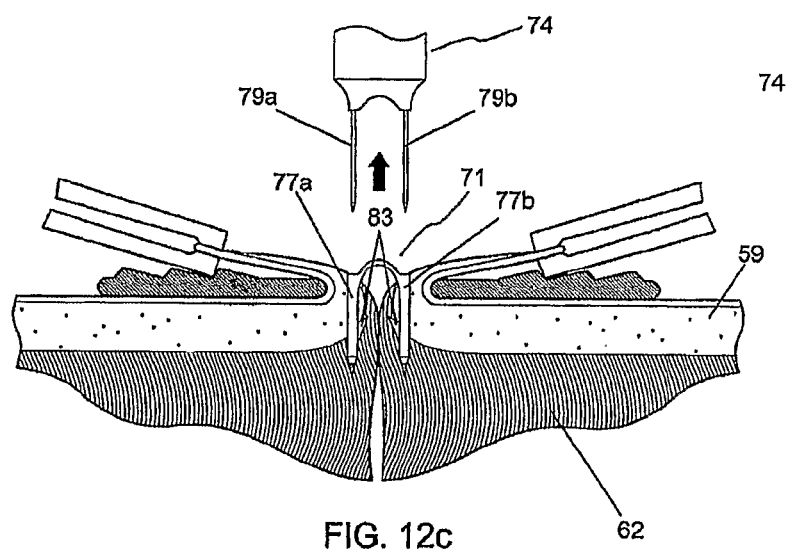
FIG. 12c shows the cross section of skin tissue as in FIG. 12b after the insertion device has been removed.

With cut surfaces 68a and 68b elevated and reflected over the apposed presser feet 306a and 306b, respectively, as shown in FIG. 10, the tissue is then ready to receive an insertion device 74 having a mounted fastener 71. The insertion device can be inserted into the tissue in a number of ways. For example, an operator can grasp insertion device 74 manually with thumb and index finger and advance it generally perpendicular to the plane or surface of the tissue as shown in FIG. 12a. After depositing the fastener 71 into cut surfaces 68a and 68b, the operator can then withdraw the insertion device 74, as shown in FIG. 12c.

Figure 11:
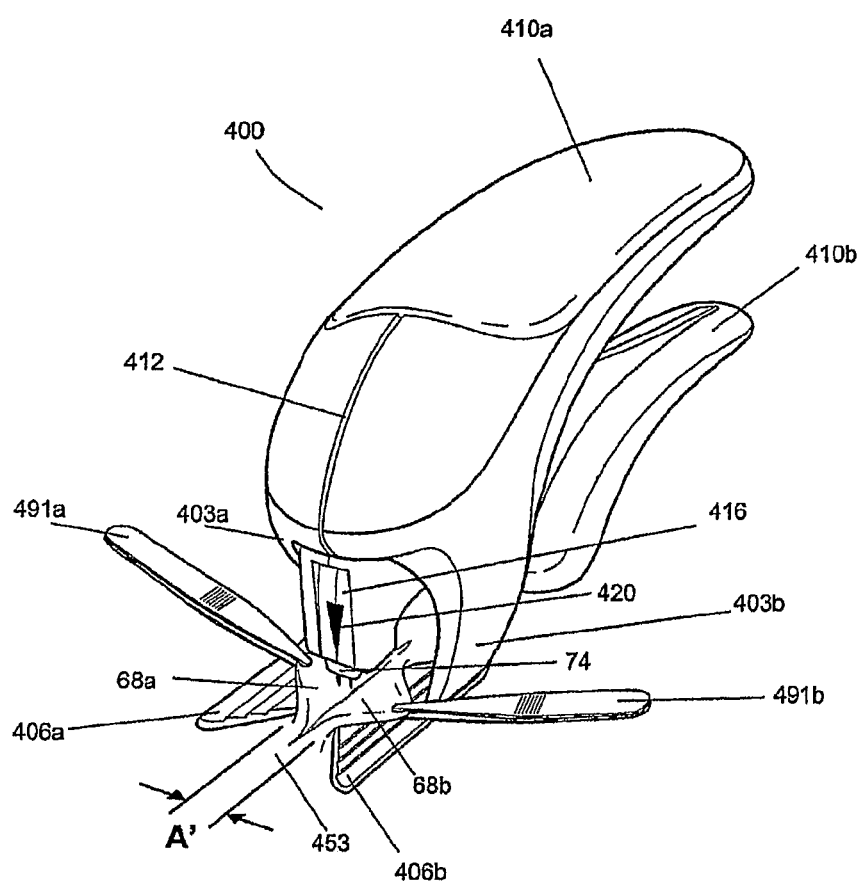
FIG. 11 is a perspective view of an alternate embodiment of a hand-held insertion mechanism used to insert the bioabsorbable fastener.

FIG. 11 is a perspective view of a hand-held insertion mechanism 400 which can hold and deploy the fastener 71 from above the plane of the tissue 453 (e.g., the skin of a human or other mammal) having the cut or incision. The insertion mechanism 400 is held in a position to place its insertion device 74 generally perpendicular to the plane or surface of the tissue having the cut or incision, as shown in FIG. 12a. The insertion mechanism 400 can have loaded into it and held internally one or more of the fasteners 71.

As shown in FIG. 11, the insertion mechanism 400 comprises a pair of opposing presser feet 406a and 406b attached to the insertion mechanism 400 via arms 403a and 403b, respectively. Arms 403a and 403b are spaced apart by gap 412 which is chosen to provide the correct gap A' between the opposing presser feet 406a and 406b. Gap 412 may be fixed by the mechanical assembly of the insertion mechanism 400 or in another embodiment gap 412 can be adjustable by a screw or other means know in the art. At least one of the presser feet 406a and 406b can have an angular or curved shape in the horizontal plane, such that the distal ends of presser feet 406a and 406b define a wider lead-in area that becomes progressively narrower from front to back, as shown in FIG. 11. The lead-in area reaches a minimum width which defines gap A' directly beneath the insertion device 74. In order to bring cut surfaces 68a and 68b into proper alignment for fastener insertion, an operator can use tissue manipulators 491a and 491b to raise cut surfaces 68a and 68b. The operator can then slide insertion mechanism 400 longitudinally along the cut, trapping and compressing the cut surfaces 68a and 68b between the fixed presser feet 406a and 406b, as shown in FIG. 11.

Alternatively, arms 403a and 403b of the insertion mechanism 400 can move in response to handles 410a and 410b to move presser feet 406a and 406b laterally into and out of the operative field. After the cut surfaces 68a and 68b are raised by the tissue manipulators 491a and 491b, the insertion mechanism 400 can be placed directly over the planned insertion site with reference to alignment mark 420, and the operator can move handles 410a and 410b through a first distance to compress presser feet 406a and 406b and align the tissue segments.

After the cut surfaces 68a and 68b of the skin tissue or other type of tissue are elevated and reflected over the fixed presser feet 406a and 406b by tissue manipulators 491a and 491b, an operator can manually compress handles 410a and 410b through a second distance, causing downward movement of the insertion device 74. As the insertion device 74 is made to move downward toward the tissue, it exits fastener cartridge 416 and penetrates the cut surfaces 68a and 68b, depositing fastener 71 (not shown). The handles 410a and 410b can be spring-loaded, so that upon release of the handles, the insertion device 74 can retract into fastener cartridge 416, leaving the embedded fastener 71 behind as shown in FIG. 12c.

The insertion mechanism 400 also can be configured to accept a plurality of the fasteners 71 held in fastener cartridge 416. In one embodiment each fastener 71 is factory installed onto a disposable insertion device 74 and the plurality of these assemblies is held in fastener cartridge 416. The assemblies of fastener 71 and insertion device 74 can be fabricated from separate components, or by an insert molding process as described previously with reference to FIGS. 7g, 7h, and 7i. The insertion mechanism 400 operates on the insertion devices one at a time to deploy the tissue fasteners 71 into the tissue and to store each insertion device 74 after deploying its preloaded tissue fastener 71. In another embodiment insertion mechanism 400 has one insertion device 74 and a plurality of fasteners 71 are positioned within fastener cartridge 416. The plurality of fasteners 71 may be individually placed into fastener cartridge or inserted as a molded assembly with inter-connecting frangible components 99, as shown in FIG. 7f. The frangible components 99 can be formed with and made out of the same bioabsorbable material used to form the fasteners 71. This assembly of breakaway fasteners provides ease of loading the fasteners 71 into the cartridge 416 and also provides controlled positioning of the fasteners 71 to facilitate the mechanical loading of the fastener onto the insertion device 74 for deployment. Although FIG. 7f depicts the frangible components 99 interconnecting the bridge sections 86 of the fasteners 71, the breakaway connecting components 99 can instead, or additionally, releasably connect together one or more other sections of adjacent fasteners 71.

Figure 12D:
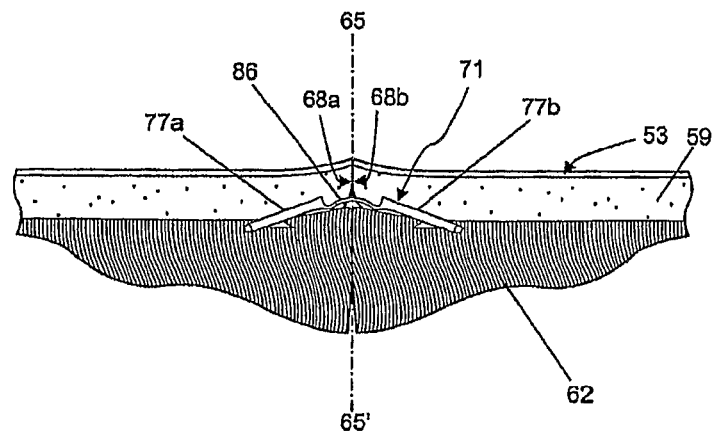
FIGS. 12d and 12e show the cross section of skin tissue as in FIG. 12c after the tissue manipulators have been removed and the bridge connecting the legs of the bioabsorbable fastener has relaxed, FIG. 12e showing a fastener with additional axially directed barbs as in FIG. 7b.
Figure 12E:
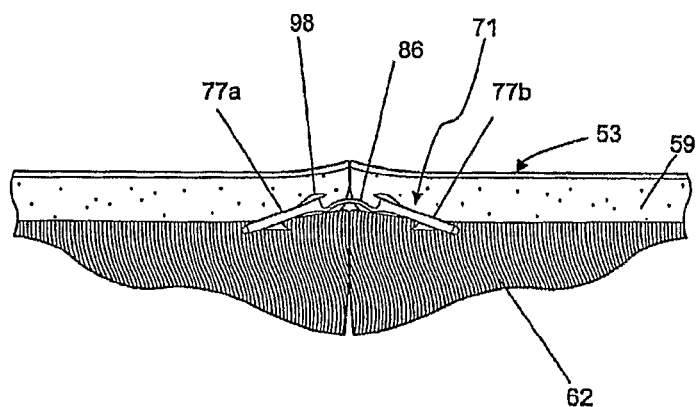

The method of deploying fastener 71 into tissue is further explained in FIG. 12a-12d. The sequence of steps is similar for an operator manually inserting individual insertion devices 74 with the aid of compressing forceps 301 or using the hand-held insertion mechanism 400. As shown in FIG. 12a, the low profile of presser feet 306a and 306b (or 406a and 406b), allows the cut surfaces 68a and 68b to be raised and retracted at an acute angle with respect to the plane of tissue 53. As shown in FIG. 12b, the acute angle of reflection of the cut surfaces 68a and 68b allows the needles 79a and 79b of insertion device 74 to enter and exit the dermis 59. As shown in FIG. 12c, as insertion device 74 is withdrawn from the tissue, the fastener 71 is left behind in the tissue by virtue of the engagement of barbs 83 of legs 77a and 77b into the dermis 59. As shown in FIG. 12d, upon release of the cut surfaces 68a and 68b and removal of the tissue manipulators 391a and 391b (or 491a and 491b), as well as presser feet 306a and 306b (or 406a and 406b), the cut surfaces 68a and 68b relax into anatomical apposition with one another. The elasticity of the tissue causes the two cut surfaces 68a and 68b to exert a distracting force against the embedded fastener 71, causing its legs 77a and 77b to spread apart, a process facilitated by the flexible bridge 86. As the legs 77a and 77b spread apart, the curvature of the flexible bridge 86 is reduced, and the distracting force places the bridge 86 in tension thereby aligning and holding legs 77a and 77b from further separation. The tensile strength of legs 77a, 77b, and bridge 86 acting on the engagement of barbs 83 with the dermis 59 holds the tissue in apposition. As shown in FIG. 12e, incorporating additional barbs 98, for example, can provide support for apposing the tissue to reduce the likelihood of the tissue receding to expose the mid-section of bridge 86 under conditions of increased distraction force. These conditions can occur, for example in skin that overlies a joint, or that is otherwise subject to frequent stretching (such as facial skin).

An advantage of the fastener 71 is that it functions by placing the legs 77a and 77b in tension with bridge 86. Various known staples, whether metal or plastic, hold the tissue in apposition by structural strength, compressive strength, or resistance to deformation. A property of plastics, such as bioabsorbable materials used in the present invention, is to be significantly stronger in tensile strength than in deformation resistance strength. Thus, for any given distracting force, the fastener 71 can be made smaller and less irritating to tissue than known fasteners.

Figure 13A:
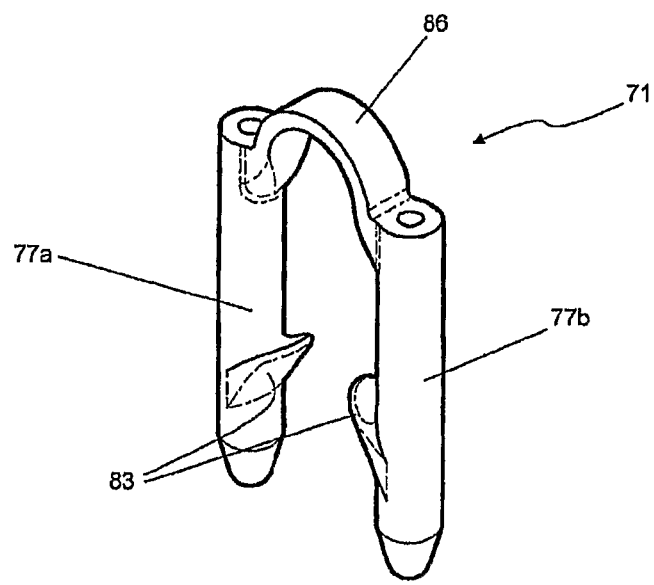
FIG. 13a shows a perspective view of an individual fastener.
Figure 13B:
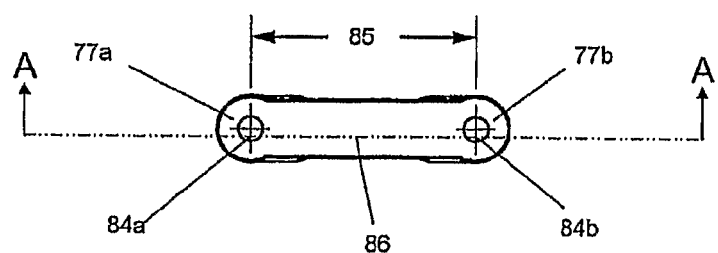
Figure 13C:
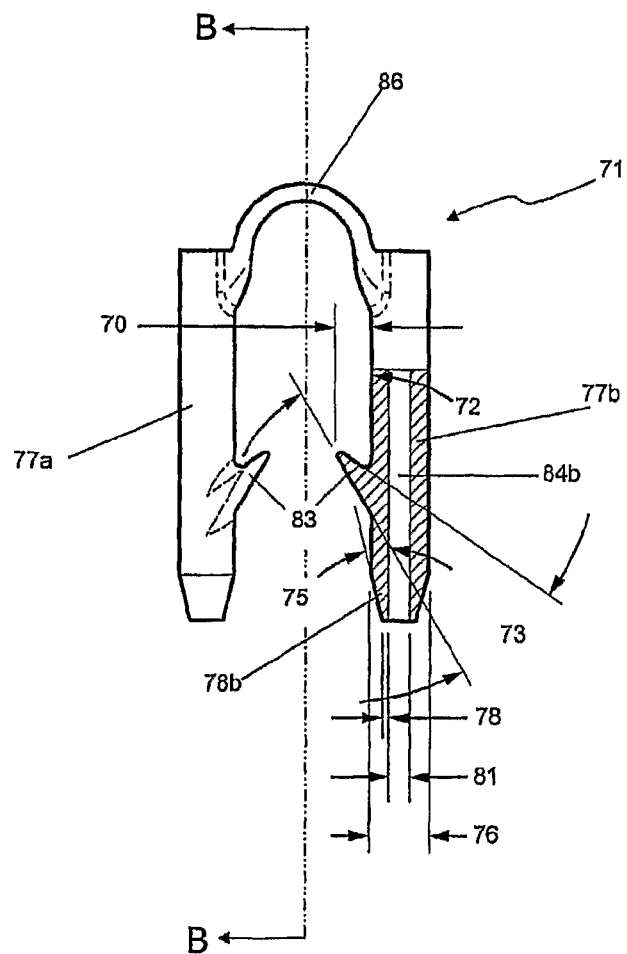
FIG. 13c shows a front view of the fastener of FIG. 13a through section A-A of FIG. 13b, and also shows a partial cutaway view of one of the legs of the fastener.
Figure 13D:
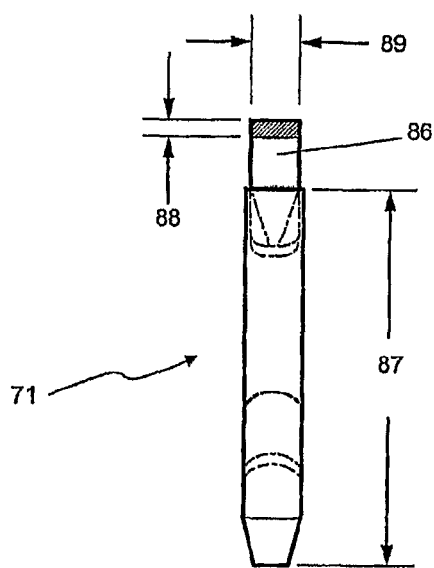
FIG. 13d shows a side view of the fastener of FIG. 13a through section B-B of FIG. 13c.

A perspective view of an embodiment of fastener 71 is shown in FIG. 13a. A top view of fastener 71 is shown in FIG. 13b. In this embodiment, the distance 85 between lumen 84a of leg 77a and lumen 84b of leg 77b is approximately 2.75 mm. Shown in FIG. 13c is a front view of fastener 71 through section A-A of FIG. 13b. A partial cutaway view of leg 77b is shown, demonstrating the dimensional relationships between leg 77b, lumen 84b and barb 83. Barb 83, for example, can form an angle 72 of approximately 30 degrees with respect to the long axis of leg 77b. In an embodiment, the effective sharpness of barb 83 can be given by angle 73, which in this case is approximately 25 degrees. The perpendicular distance 70 of the tip of barb 83 from the surface of leg 77b in this embodiment is approximately 0.6 mm. The amount by which the distal portion 78b of leg 77b tapers inwardly can be determined by angle 75, which in this embodiment is approximately 15 degrees. In the fastener 71 of FIG. 13c, the overall width 76 of leg 77b is approximately 0.8 mm, the diameter 81 of lumen 84b is approximately 0.3 mm, and the radial thickness of the wall of leg 77b tapers from approximately 0.25 mm to approximately 0.075 mm at its tip 78. FIG. 13d is a side view of fastener 71, through section B-B of FIG. 13c. In this embodiment, the overall length 87 of legs 77a and 77b is approximately 5.25 mm. The cross-sectional rectangular shape of bridge 86 of this embodiment is also apparent in this view, a shape that contributes to the lateral flexibility of the bridge. The bridge 86 of FIG. 13d has a vertical thickness 88 of approximately 0.25 mm and a transverse thickness 89 of approximately 0.7 mm.

Embodiments of fasteners according to the invention, such as the disclosed fastener 71, can be manufactured from one or more bioabsorbable materials, such as copolymers of L-Lactide or D,L-Lactide, and Glycolide. Any suitable bioabsorbable material(s) can be used to form the fastener 71, as long as the material(s) can be formed into the fastener 71 and perform as disclosed herein.

The terms bioabsorbable and bioabsorbable material as used herein are intended to include any suitable material(s) for fasteners according to the invention that hold their shape and are stable outside of the body but that degrade, resorb, absorb, erode, and/or otherwise breakdown within the body of a patient over time and are eliminated by the body's normal functions.

A fastener made of a poly(lactic-glycolic) acid ("PLGA") copolymer, for example, can have a ratio of L-lactide to Glycolide of from about 10:90 to about 95:5 by weight, such as for example 80:20, 82:18, or 85:15.

In some embodiments, the bioabsorbable material used for the fastener 71 is a lactide/glycolide copolymer (such as, for example, poly-DL-Lactide-co-Glycolide or "PDLGA") where the ratio is never less than at least 10% of one element and, in a more specific embodiment, is in a range of 60%-70% lactide.

Some of the bioabsorbable materials that could be used to form a fastener according to the invention include poly(dl-lactide), poly(l-lactide), polyglycolide, poly(dioxanone), poly(glycolide-co-trimethylene carbonate), poly(1-lactide-co-glycolide), poly(d1-lactide-co-glycolide), poly(1-lactide-co-d1-lactide), poly(glycolide-co-trimethylene carbonate-co-dioxanone), caprolactone, ploydioxane, and/or copolymers of L-Lactide or D,L-Lactide, and Glycolide.

The material used for the fastener 71 could include compositions with naturally occurring biopolymers such as collagen and elastin, or stainless steel, metal, nylon or any other biocompatible materials in the case of a non-absorbable fastener, or even various combinations of such materials depending upon the desired application and performance of the fastener 71.

Different formulations of bioabsorbable polymers can provide different strength versus dissolution profiles. In one embodiment, a bioabsorbable fastener according to the present invention is formed of a polymer, or a formulation of polymers, which provides a tensile breaking strength from leg 77a to leg 77b across bridge 86 of about 3.5 lbs. upon initial deployment into a patient and maintains that breaking strength at or above about 2 lbs. for a minimum of about 5 days. A fastener made of PLGA having a ratio of L-lactide to Glycolide of about 82:18 and having a bridge of a rectangular cross-section of about 0.25 mm high and about 0.8 mm wide can have such force-withstanding properties.

Depending on the type of opening or wound being held together within the body of the patient with one or more of the fasteners 71 according to the invention, each of the fasteners 71 will be formed in such a way and of one or more bioabsorbable materials suitable to allow the fastener 71 to maintain its structural integrity within the body of the patient for about 14 days or for a minimum of about 5 days. The specific time it takes for any particular fastener to be bioabsorbed in any particular application within the body of a patient typically will vary and is a function of the bioabsorbable material(s) used to form the fastener, the fastener's precise shape, the area within the body of the patient where the fastener is deployed, and the patient himself or herself.

The disclosed embodiments according to the invention are exemplary and illustrative. The invention is not limited by or only to the disclosed embodiments. Various alternatives, modifications, and combinations not necessarily expressly described herein in connection with any particular disclosed embodiments are considered part of this disclosure and within the scope of this disclosure.

What is claimed is:

1. A tissue fastening system for use in closing two sides of an incision or wound in a surface of skin tissue, comprising:
   a tissue fastener comprising (i) a bridge section including a first portion and a second portion, (ii) a first leg section integral with the bridge section and extending from the first portion of the bridge section, at least a portion of the first leg section defining a first lumen extending therethrough such that the first leg section is cannulated, and (iii) a second leg section integral with the bridge section and extending from the second portion of the bridge section, at least a portion of the second leg section defining a second lumen extending therethrough such that the second leg section is cannulated, each of the first and second leg sections including at least one barb extending from that leg section, each of the barbs including a pointed element and arranged to be oriented such that its pointed element is not directed towards the surface of the skin tissue and such that the barb resists dislodgement of the fastener after the fastener is deployed into the skin tissue and completely below the surface of the skin tissue, the bridge section being sufficiently flexible to allow the first and second leg sections to spread apart angularly, the bridge section and the first and second leg sections comprising a single piece of material; and a hand-held insertion mechanism comprising first and second presser feet for everting and reflecting thereover each of the two sides of the incision or wound respectively, the hand-held insertion mechanism also comprising an insertion device arranged to move and deploy the tissue fastener in a generally perpendicular orientation in relation to a plane defined by bottom surfaces of the presser feet to deploy the fastener into the two sides of the incision or wound, the insertion device comprising a first needle configured to extend through the first lumen of the cannulated first leg section and a second needle configured to extend through the second lumen of the cannulated second leg section, the first and second needles being substantially parallel to each other, each of the first and second needles including a sharp end that is exposed with the tissue fastener loaded onto the insertion device, the sharp ends for penetrating into the skin tissue, the hand-held insertion mechanism arranged to drive at least a portion of the insertion device into the skin tissue and then retract the insertion device to dispose the tissue fastener completely below the surface of the skin tissue.

2. The system of claim 1, wherein the tissue fastener is preloaded onto the insertion device.

3. The system of claim 1, wherein the first and second presser feet are movable and are separated by a predetermined distance when the presser feet are moved to their fullest extent toward each other.

4. The system of claim 1 wherein the skin tissue is human skin tissue.

5. The system of claim 1 wherein the single piece of material is bioabsorbable.

6. The system of claim 5 wherein the bioabsorbable material comprises a copolymer.

7. The system of claim 5 wherein the bioabsorbable material comprises a blend of polymers.

8. The system of claim 1 wherein the bridge section comprises a frangible connector for releasably connecting the bridge section to another fastener.

9. The system of claim 8 wherein the frangible connector is formed with and made out of the same material as the bridge section.

10. The system of claim 1 wherein, with the fastener loaded onto the insertion device, the at least one barb of the first leg section of the fastener faces the at least one barb of the second leg section of the fastener.

* * * * *